United States Patent
Kuroshima

(10) Patent No.: US 8,182,759 B2
(45) Date of Patent: May 22, 2012

(54) ENDOSCOPE WASHING AND DISINFECTING APPARATUS AND LIQUID SUPPLY MOUTHPIECE

(75) Inventor: Hisashi Kuroshima, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 374 days.

(21) Appl. No.: 12/494,996

(22) Filed: Jun. 30, 2009

(65) Prior Publication Data

US 2010/0004510 A1    Jan. 7, 2010

(30) Foreign Application Priority Data

Jul. 2, 2008 (JP) ................. 2008-173832

(51) Int. Cl.
    *A61L 2/00* (2006.01)
    *A61B 1/00* (2006.01)
    *A61B 1/12* (2006.01)
(52) U.S. Cl. ................ 422/292; 600/158; 600/104
(58) Field of Classification Search .............. 422/292; 600/158, 104
See application file for complete search history.

(56) References Cited

U.S. PATENT DOCUMENTS

| 4,667,655 A * | 5/1987 | Ogiu et al. .............. 600/132 |
| 5,833,935 A | 11/1998 | Malchesky |
| 2005/0209507 A1 * | 9/2005 | Suzuki et al. ........... 600/133 |

FOREIGN PATENT DOCUMENTS

| JP | 08-024813 | 1/1996 |
| JP | 2001-299697 | 10/2001 |

* cited by examiner

*Primary Examiner* — Kevin Joyner
(74) *Attorney, Agent, or Firm* — Scully, Scott, Murphy & Presser, P.C.

(57) ABSTRACT

An endoscope washing and disinfecting apparatus of the present invention includes a first channel member in which a projection portion abuts on a fitting surface in a channel mouthpiece, and a first channel internally provided communicates with a suction channel inside the channel mouthpiece, a second channel member which is fitted and fixed to an outer periphery of the first channel member, and is internally provided with a second channel which communicates with the first channel, a pressing member which is provided in the second channel, and presses the first channel member to the channel mouthpiece side in the second channel, and a liquid introduction port which is formed in the second channel member and introduces a liquid to the second channel.

14 Claims, 6 Drawing Sheets

ENDOSCOPE WASHING AND DISINFECTING APPARATUS AND LIQUID SUPPLY MOUTHPIECE

This application claims benefit of Japanese Application No. 2008-173832 filed in Japan on Jul. 2, 2008, the contents of which are incorporated by this reference.

BACKGROUND OF THE INVENTION

1. Field of the Invention

The present invention relates to an endoscope washing and disinfecting apparatus which automatically washes and disinfects an endoscope channel by fitting a liquid supply mouthpiece which supplies at least a liquid to the endoscope channel to a channel mouthpiece of the endoscope channel of an endoscope, and the liquid supply mouthpiece.

2. Description of the Related Art

In recent years, endoscopes have been widely used in the medical field and the industrial field. With the endoscopes used in the medical field, the elongated insertion portions are inserted into body cavities, whereby organs in body cavities can be observed, and various treatments can be performed with use of treatment instruments inserted into the insertion channels for the treatment instruments included by the endoscopes in accordance with necessity.

The endoscopes of the medical field are used by being inserted into body cavities especially for the purpose of inspection and treatment, and therefore, the endoscopes need to be washed and disinfected after use to be used again. As the method for washing and disinfecting the endoscopes already used, there is known, for example, the method with use of an endoscope washing and disinfecting apparatus (hereinafter, simply called a washing and disinfecting apparatus).

With use of the washing and disinfecting apparatus, an endoscope can be automatically washed, disinfected, rinsed, drained and the like (hereinafter, called a washing and disinfecting process) by only being set in a washing and disinfecting bath of the washing and disinfecting apparatus.

On this occasion, a washing solution and a disinfectant solution are supplied not only to an outer surface of the endoscope, but also into a plurality of endoscope channels such as a known gas supply and water supply channel, suction channel, and a treatment instrument insertion channel which the endoscope has inside, and thereby, the insides of the endoscope channels are washed and disinfected.

In washing and disinfecting the inside of an endoscope channel using a washing and disinfecting apparatus, a liquid supply mouthpiece provided at the other end of a washing tube is fitted to a channel mouthpiece of the endoscope channel of the endoscope which is set in a washing and disinfecting bath by, for example, an operator. A liquid supply port which is provided in the washing and disinfecting apparatus is connected to one end of the washing tube. As a result, washing and disinfection are performed in the state in which various liquids such as a washing solution, a disinfectant solution, and a rinse water can be supplied into the endoscope channel via the washing tube from the washing and disinfecting apparatus.

Incidentally, when a tissue in a body cavity which is sucked in an inspection using, for example, an endoscope is clogged in the endoscope channel, the abovementioned various liquids cannot be supplied to the entire inside of the endoscope channel due to the tissue with which the endoscope channel is clogged.

Therefore, it is conventionally checked visually by an operator whether or not there is clogging in the endoscope channel. However, a visual observation operation becomes not only a burden for an operator, but also it is difficult to visually recognize clogging in an endoscope channel reliably.

Thus, Japanese Patent Application Laid-Open Publication No. 2001-299697 discloses the configuration in which a flow rate sensor is provided for each of the channels which supply various kinds of liquids in the liquid supply port of the washing and disinfecting apparatus. Specifically, there is disclosed the configuration in which clogging in an endoscope channel can be detected by comparing the flow rate when the inside of the endoscope channel is clogged, and the flow rate without clogging in the endoscope channel, more specifically, the configuration in which when the detected flow rate is lower than the flow rate without clogging in the endoscope channel, clogging inside the endoscope channel is detected by the flow rate sensor.

However, when a liquid supply mouthpiece is not fitted to the channel mouthpiece of an endoscope channel to be completely fluid-tight, a liquid leaks from between both the mouthpieces when various liquids are supplied into the endoscope channel.

Thereby, even if clogging occurs in the endoscope channel, various liquids leak from between the respective mouthpieces. Therefore, there is the problem that though various kinds of liquids are not supplied to the entire inside of the endoscope channel, decrease in flow rate by the flow rate sensor cannot be detected, and clogging of the endoscope channel cannot be detected.

In view of such a problem, there is known the configuration being capable of connecting the respective mouthpieces to be fluid-tight, but in such a configuration, seal portions in the respective mouthpieces do not contact the washing solution and the disinfectant solution, and therefore, washing and disinfection of the seal portions in the respective mouthpieces have to be performed additionally in the subsequent process, which is very complicated for an operator.

Japanese Patent Application Laid-Open Publication No. 8-24813 discloses a configuration of connection of mouthpieces in which when the liquid supply mouthpiece is fitted to the channel mouthpiece of an endoscope channel, predetermined amounts of various liquids leak from a space between the respective mouthpiece portions, and by the leaked various kinds of liquids, seal portions in the respective mouthpiece portions can be washed and disinfected.

SUMMARY OF THE INVENTION

Briefly, an endoscope washing and disinfecting apparatus of the present invention is an endoscope washing and disinfecting apparatus which automatically washes and disinfects an endoscope channel by fitting a liquid supply mouthpiece which supplies at least a liquid to the endoscope channel to a channel mouthpiece of the endoscope channel of an endoscope, and the liquid supply mouthpiece includes a first channel member in which a part of the first channel member abuts on a fitting surface in the channel mouthpiece, and a first channel internally provided communicates with the endoscope channel inside the channel mouthpiece, when the liquid supply mouthpiece is fitted onto the channel mouthpiece, a second channel member which is fitted and fixed to an outer periphery of the first channel member, and is internally provided with a second channel which communicates with the first channel, a pressing member which is provided in the second channel, and presses the first channel member to the channel mouthpiece side in the second channel when the liquid supply mouthpiece is fitted onto the channel mouthpiece, and a liquid introduction port which is formed in the second channel member and introduces the liquid into the second channel.

Further, a liquid supply mouthpiece includes a first channel member in which a part of the first channel member abuts on a fitting surface in a channel mouthpiece, and a first channel internally provided communicates with an endoscope channel in the channel mouthpiece when the liquid supply mouthpiece is fitted onto the channel mouthpiece of the endoscope channel of an endoscope, a second channel member which is fitted on and fixed to an outer periphery of the first channel member and is internally provided with a second channel which communicates with the first channel, a pressing member which is provided in the second channel, and presses the first channel member to the channel mouthpiece side in the second channel when the liquid supply mouthpiece fitted to the channel mouthpiece, and a liquid introduction port which is formed in the second channel member and introduces the liquid into the second channel.

The above and other objects, features and advantages of the invention will become more clearly understood from the following description referring to the accompanying drawings.

DETAILED DESCRIPTION OF THE PREFERRED EMBODIMENTS

Hereinafter, embodiments of the present invention will be described with reference to the drawings. Hereinafter, an endoscope channel provided in an endoscope will be described with a suction channel also used as a treatment instrument inserting channel which sucks a target object of an examined region being cited as an example.

Figure 1:
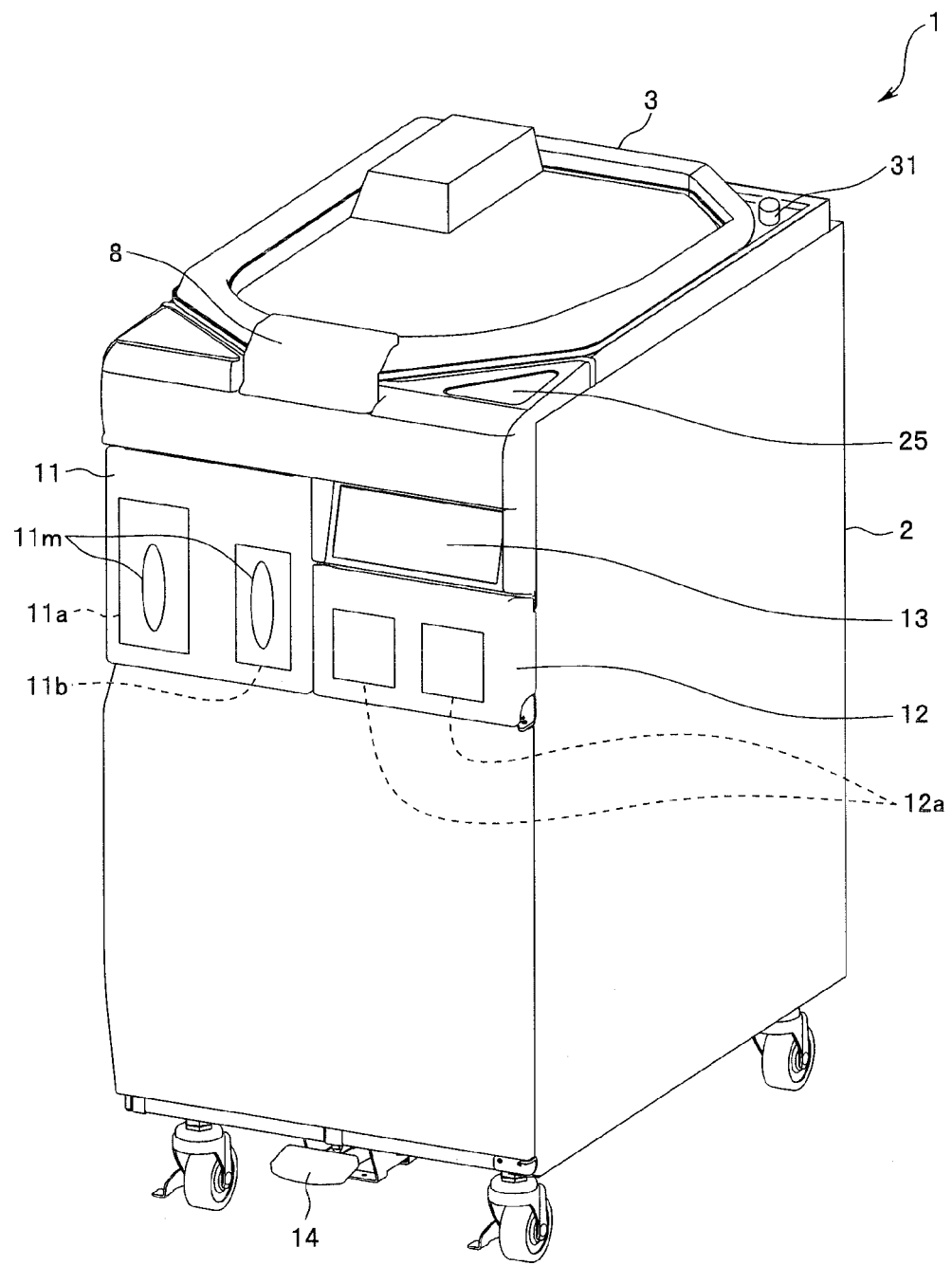
FIG. 1 is a perspective view of a washing and disinfecting apparatus showing the present embodiment.
Figure 2:
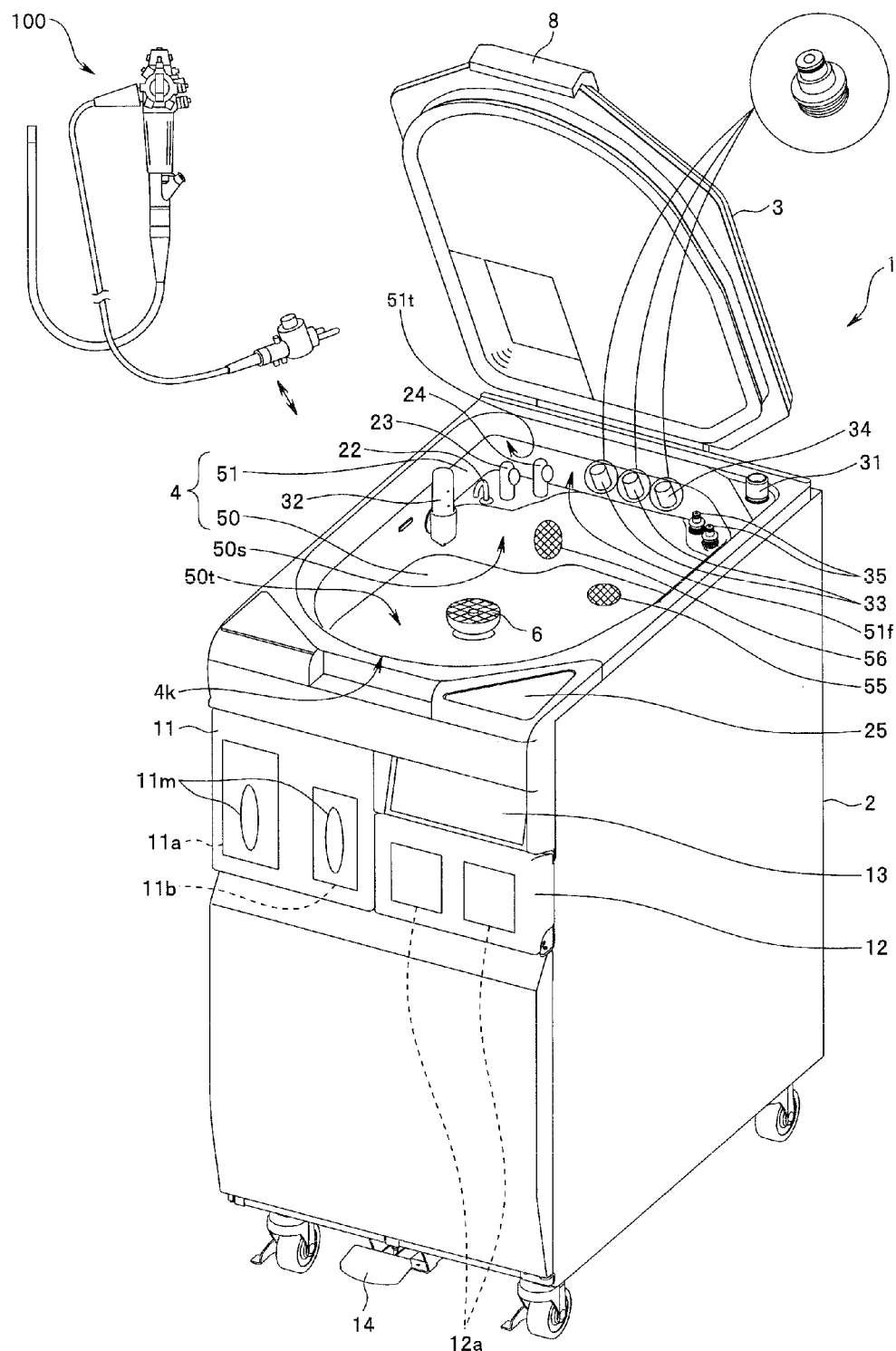
FIG. 2 is a perspective view of the washing and disinfecting apparatus showing a state in which a top cover of FIG. 1 is opened, and an endoscope can be housed in a washing and disinfecting bath.

FIG. 1 is a perspective view of a washing and disinfecting apparatus showing the present embodiment, and FIG. 2 is a perspective view of a washing and disinfecting apparatus showing a state in which a top cover of FIG. 1 is opened, and an endoscope can be housed in a washing and disinfecting bath.

As shown in FIGS. 1 and 2, a washing and disinfecting apparatus 1 is an apparatus for washing and disinfecting an endoscope 100 which is already used, and a main part is configured by an apparatus main body 2, and a top cover 3 connected to an upper portion of the apparatus main body 2 via, for example, a hinge not illustrated to be openable and closeable.

As shown in FIG. 1, in a state in which the top cover 3 is closed to the apparatus main body 2, the apparatus main body 2 and the top cover 3 are configured to be fixed by, for example, a latch 8 which is placed at a position in which the apparatus main body 2 and the top cover 3 are opposed to each other.

A detergent/alcohol tray 11 is placed at an upper portion of a left half part in FIG. 1, for example, which is on a front surface in FIG. 1 which an operator of the apparatus main body 2 approaches (hereinafter, called a front surface) to be able to be drawn forward of the apparatus main body 2.

A detergent tank 11a in which a detergent which is used when the endoscope 100 is washed is stored, and an alcohol tank 11b in which alcohol which is used when the endoscope 100 after washing and disinfection is dried is stored are housed in the detergent/alcohol tray 11. Since the detergent/alcohol tray 11 can be drawn, a liquid can be supplied to each of the tanks 11a and 11b in a predetermined way.

The detergent/alcohol tray 11 is provided with two window portions 11m, so that from the window portions 11m, residual amounts of the detergent and alcohol poured into the respective tanks 11a and 11b can be checked by an operator. The detergent is a concentrated detergent which is diluted to a predetermined concentration by tap water which is subjected to filtering treatment by a supply water filter 17 (see FIG. 3) which will be described later. In the present embodiment, a mixed solution of the detergent and tap water will be called a washing solution in the following description.

Further, at an upper portion of a right half part in FIG. 1, for example, which is on the front surface of the apparatus main body 2, a cassette tray 12 is placed to be capable of being drawn forward of the apparatus main body 2. A chemical solution bottle 12a filled with a disinfectant solution such as peracetic acid, for example, which is used when the endoscope 100 is disinfected, is housed in the cassette tray 12. Since the cassette tray 12 is capable of being drawn, the chemical solution bottle 12a can be set in a predetermined way.

Further, a sub operation panel 13 on which display of washing and disinfecting time, an instruction button for heating the disinfectant solution and the like are placed is placed at an upper portion of the cassette tray 12, which is on the front surface of the apparatus main body 2.

Further, a pedal switch 14 for opening the top cover 3 which is closed on the upper portion of the apparatus main body 2 upward of the apparatus main body 2 as shown in FIG. 2 by a depressing operation of the operator is placed at a lower portion of the front surface in FIG. 1 of the apparatus main body 2.

Further, as shown in FIG. 2, a main operation panel 25 on which setting switches such as a washing and disinfecting operation start switch of the apparatus main body 2, and a washing and disinfecting mode selection switch are placed is provided near both ends at a front surface side in FIG. 2 which, for example, the operator approaches, of a top surface of the apparatus main body 2.

Further, a water supply hose connection port 31 for supplying tap water to the apparatus main body 2 is placed at a back surface side opposed to the front surface which the operator approaches, which is on the top surface of the apparatus main body 2. A water supply hose 31*a* (see FIG. 3) which will be described later and is connected to a faucet 5 (see FIG. 3) which will be described later is connected to the water supply hose connection port 31. A mesh filter which filters tap water may be placed in the water supply hose connection port 31.

Figure 3:
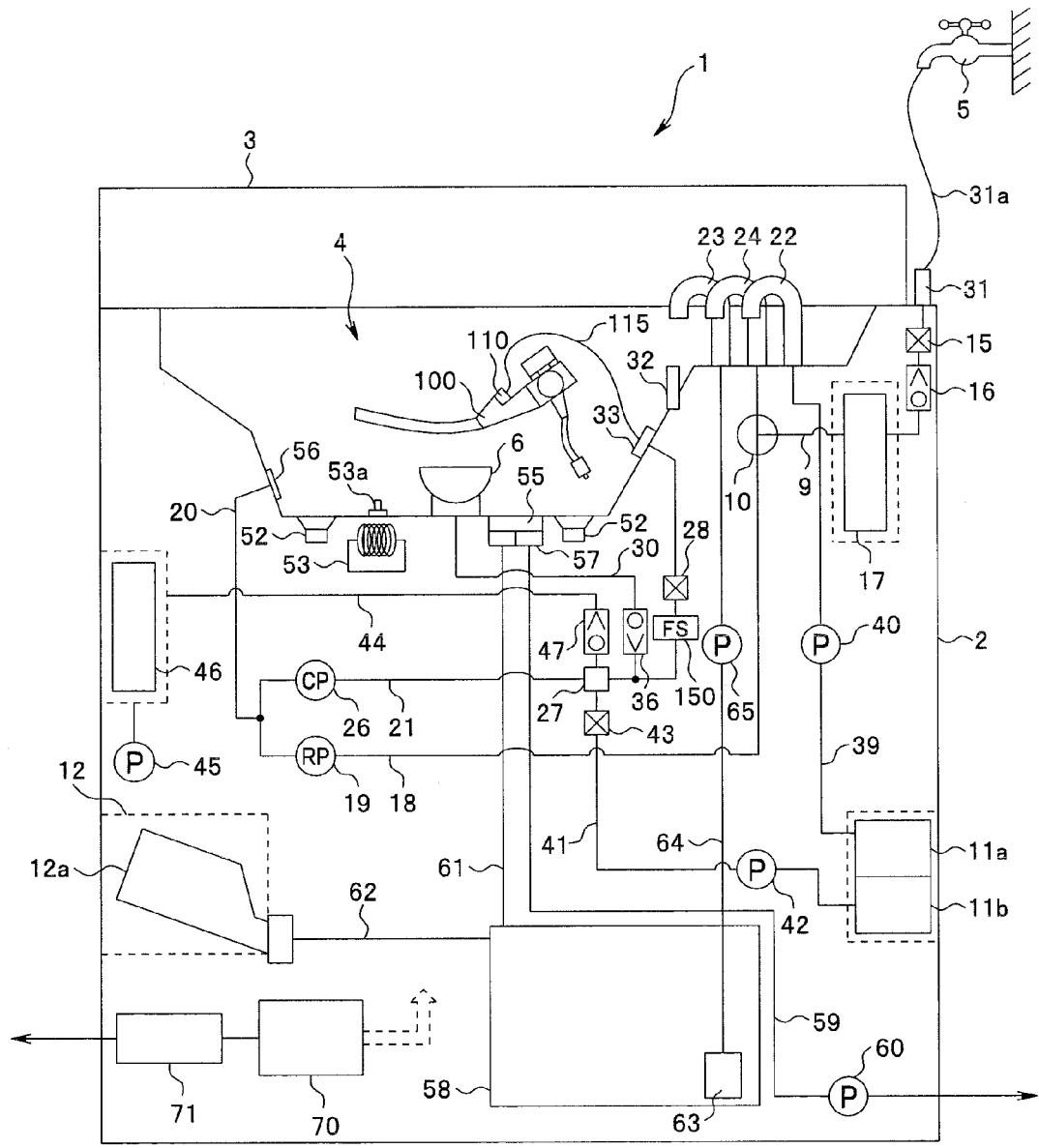
FIG. 3 is a diagram showing an internal configuration of the washing and disinfecting apparatus of FIG. 1, in a state in which an endoscope is housed in the washing and disinfecting bath.

Further, a washing and disinfecting bath 4 which is capable of housing the endoscope 100 as shown in FIG. 3 which will be described later, with an endoscope housing port being opened and closed by the top cover 3, is provided at a substantially central portion of the top surface of the apparatus main body 2. The washing and disinfecting bath 4 is configured by a bath main body 50 and a terrace portion 51 continuously provided circumferentially at an outer peripheral edge of the endoscope housing port of the bath main body 50.

The bath main body 50 is capable of housing the endoscope 100 when the endoscope 100 after use is washed and disinfected, and a drain port 55 for draining a washing solution, water, alcohol, a disinfectant solution and the like which are supplied to the bath main body 50 from the bath main body 50 is provided at a bottom surface 50*t* of the bath main body 50.

Further, a circulation port 56 for supplying the water, washing solution, disinfectant solution and the like which are supplied to the bath main body 50 to a suction channel 100*i* (see FIG. 4), which will be described later and is included inside the endoscope 100, via means which will be described later is provided at an optional position of a peripheral side surface 50*s* of the bath main body 50. Further, the circulation port 56 also has a function of supplying the washing solution, water, disinfectant solution and the like supplied to the bath main body 50 into the bath main body 50 again from a water supply circulation nozzle 24 which will be described later through a mesh filter or the like. Further, a mesh filter for filtering the washing solution or the like may be provided in the circulation port 56.

The aforementioned circulation port 56 may be provided at the bottom surface 50*t* of the bath main body 50. If the circulation port 56 is provided at the bottom surface 50*t* of the bath main body 50, the timing for supplying the various liquids to the suction channel 100*i* of the endoscope 100, or the bath main body 50 again can be advanced. Further, when the user replaces the mesh filter or the like provided in the circulation port 56, if the circulation port 56 is provided at the bottom surface 50*t*, there is provided the advantage of the operator easily approaching the circulation port 56.

An ultrasound transducer 52 which will be described later, a heater 53 (see FIG. 3 for both of them) are further placed in the bath main body 50 of the washing and disinfecting bath 4, and a washing case 6 is placed at a substantially central portion of the bottom surface 50*t* of the bath main body 50. The ultrasound transducer 52 gives vibration to the washing water stored in the washing and disinfecting bath 4 or tap water to apply ultrasound washing to or rinse the outer surface of the endoscope 100. Further, the heater 53 heats the disinfectant solution, tap water or the like stored in the washing and disinfecting bath 4 to a predetermined temperature.

The washing case 6 houses buttons such as the scope switches of the endoscope 100, and replaceable components attached to the endoscope 100. As a result, the respective buttons and the detached components are washed and disinfected together with the endoscope 100.

A water level sensor 32 with a cover which detects water levels of the washing solution, water, disinfectant solution and the like supplied to the bath main body 50 is provided at an optional position of the side surface 50*s* of the bath main body 50.

On a surface other than the terrace surface 51*t* of the terrace portion 51, that is, on a surface parallel with the bottom surface 50*t* of the bath main body 50, a detergent nozzle 22 and a disinfectant solution nozzle 23 are placed. The detergent nozzle 22 supplies the detergent which is diluted to a predetermined concentration by tap water by a detergent pump 40 which will be described later (see FIG. 3) from the detergent tank 11*a* to the bath main body 50, whereas the disinfectant solution nozzle 23 supplies the disinfectant solution by a chemical solution pump 65 (see FIG. 3) which will be described later from a chemical solution tank 58 (see FIG. 3) which will be described later to the bath main body 50.

Further, on the surface parallel with the bottom surface 50*t* of the bath main body 50, of the terrace portion 51, the water supply circulation nozzle 24 for supplying water to the bath main body 50 is placed. The water supply circulation nozzle 24 also has the function of supplying the washing solution, water, disinfectant solution and the like sucked from the circulation port 56 of the bath main body 50 to the bath main body 50 again.

The detergent nozzle 22, the disinfectant solution nozzle 23 and the water supply circulation nozzle 24 may be placed on the terrace surface 51*t*.

Further, a plurality of, in this case, two gas supply and water supply/forceps opening ports 33 for supplying water, the washing solution, alcohol, disinfectant solution, air or the like to a plurality of endoscope channels included in the endoscope 100, a forceps raiser port 34, and a leakage water detecting port 35, which will be described later, are placed on a surface 51*f* at the side opposed to an operator approaching position 4*k*, of the terrace surface 51*t* of the terrace portion 51.

Figure 4:
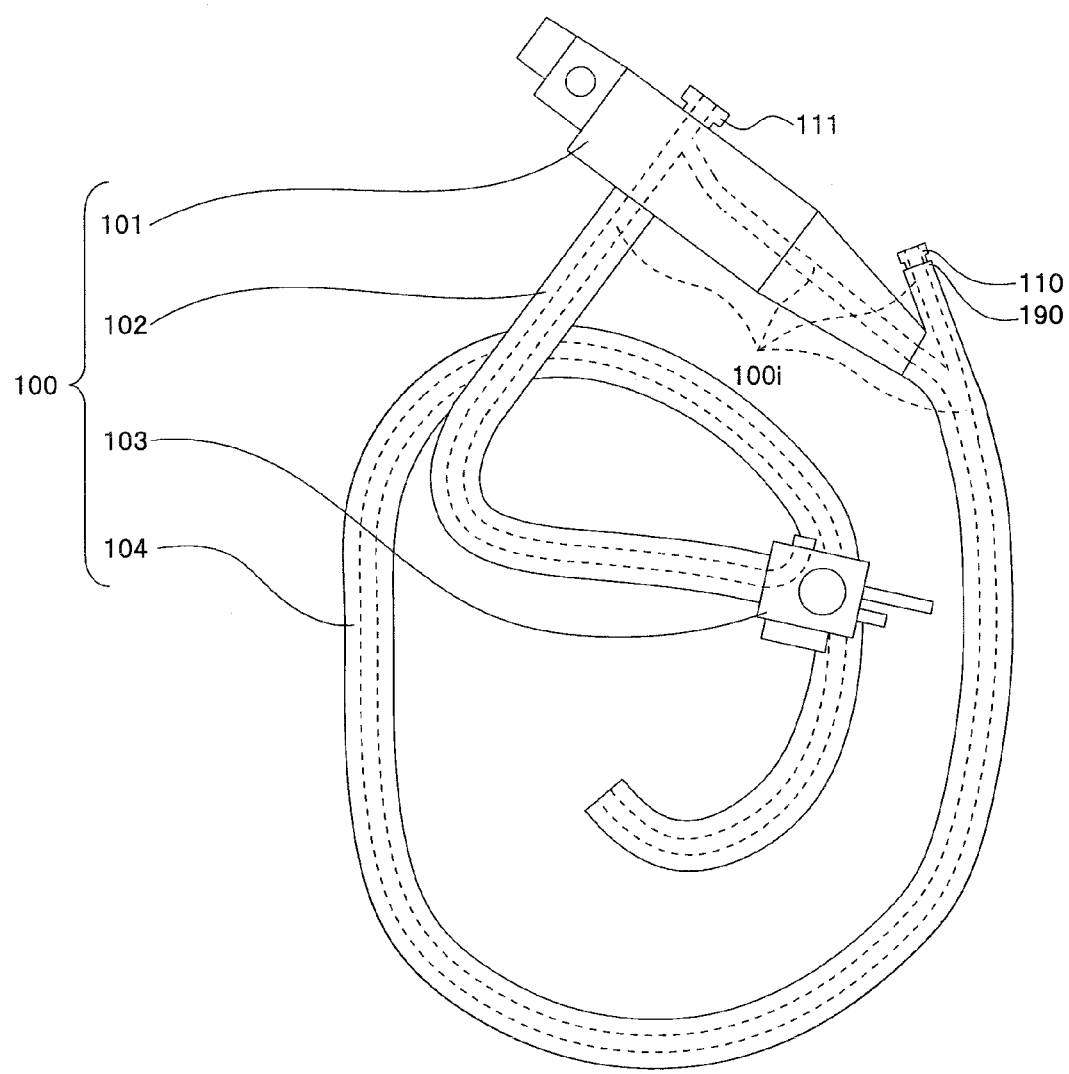
FIG. 4 is a view schematically showing the endoscope housed in the washing and disinfecting bath of FIG. 3 in enlargement.

Next, on the basis of FIGS. 3 and 4, an internal configuration of the washing and disinfecting apparatus 1 will be described. FIG. 3 is a diagram showing the internal configuration of the washing and disinfecting apparatus of FIG. 1, in a state in which an endoscope is housed in the washing and disinfecting bath, and FIG. 4 is a view schematically showing the endoscope housed in the washing and disinfecting bath of FIG. 3 in enlargement.

As shown in FIG. 3, the washing and disinfecting apparatus 1 has the configuration in which the water supply hose connection port 31 is connected to one end of the water supply hose 31*a*, and the other end of the water supply hose 31*a* is connected to the external faucet 5, whereby tap water is supplied.

The water supply hose connection port 31 communicates with one end of a water supply channel 9. The water supply channel 9 has the other end connected to a three-way electromagnetic valve 10, and in the middle of the channel, a water supply electromagnetic valve 15, a check-valve 16, and a supply water filter 17 are interposed in sequence from a side of the water supply hose connection port 31.

The supply water filter 17 is configured as a cartridge type filter so as to be regularly replaced, and is attachable and detachable to and from a filter case not illustrated. The supply water filter 17 removes foreign matters, various bacteria and the like in the tap water which pass through the supply water filter 17.

The three-way electromagnetic valve 10 is connected to one end of a liquid flow channel 18, and switches communication of the water supply channel 9 and the liquid flow channel 18 with the water supply circulation nozzle 24 by an internal valve. Namely, the water supply circulation nozzle 24 communicates with either one of the water supply channel 9 and the liquid flow channel 18 by the switching operation of the three-way electromagnetic valve 10. Further, a liquid flow pump 19 which is a non-self-priming pump capable of transferring only a liquid and excellent in liquid transfer ability is interposed at the other end side of the liquid flow channel 18.

One end of the circulation channel 20 which is a liquid supply channel is connected to the circulation port 56 placed in the washing and disinfecting bath 4. The other end of the circulation channel 20 is branched into two so as to communicate with the other end of the liquid flow channel 18 and one end of a channel 21 which is a fluid supply channel. The other end of the channel 21 communicates with the aforementioned respective gas supply and water supply/forceps opening ports 33 (in FIG. 3, only one of the respective gas supply and water supply/forceps opening ports 33 is illustrated). Though not illustrated, the other end of the channel 21 also communicates with the aforementioned forceps raiser port 34.

Further, one end of a washing tube 115 which is a liquid supply channel is connected to the port 33, and the other end of the washing tube 115 is connected to a channel mouthpiece 110 provided in a treatment instrument inserting port 190 of an operation section 101 and a channel mouthpiece 111 provided at the operation section 101 in the endoscope 100 as shown in FIG. 4. The channel mouthpieces 110 and 111 are mouthpieces which communicate with the suction channel 100i inserted through the insides of the operation section 101, an insertion section 104, a universal cord 102 and a connector 103.

Further, examples of a channel diameter of the suction channel 100i are that the channel diameter of the suction channel 100i which is inserted through the insides of the insertion section 104 and the operation section 101, for example, is 1.2 to 6.0 mm, and the channel diameter of the suction channel 100i which is inserted through the insides of the universal cord 102 and the connector 103 is 3.7 mm.

A connection configuration at the other end side of the washing tube 115 to the channel mouthpiece 110 will be described later. Further, the other end of a washing tube not illustrated with one end connected to the forceps raiser port 34 is also connected to the channel mouthpiece 111 though not illustrated.

In the channel 21, a channel pump 26, a channel block 27, a flow rate sensor 150 and a channel electromagnetic valve 28 are respectively interposed in sequence from the aforementioned one end side, in the middle of the channel. The other end of a case channel 30 with one end connected to the washing case 6 is connected to the channel 21 between the channel block 27 and the channel electromagnetic valve 28. In the case channel 30, a relief valve 36 is interposed.

The channel pump 26 is configured by a self-priming pump capable of transferring either gas or liquid at a higher pressure than a non-self-priming pump. The reason why the channel pump 26 is configured by a self-priming pump is that in order to perform washing, disinfection, rinse and the like reliably for the inside of the suction channel 100i included by the endoscope 100, a washing solution, disinfectant solution, tap water, air and the like need to be fed into the suction channel 100i from the port 33 via the channel 21 at a high pressure.

The flow rate sensor 150 detects a supply rate of the liquid flowing in the channel 21, and also detects clogging of the suction channel 100i of the endoscope 100 from the supply rate of the liquid.

The detergent nozzle 22 is connected to one end of a detergent channel 39, and the other end of the detergent channel 39 is connected to the detergent tank 11a. In the detergent channel 39, a detergent pump 40 configured by a self-priming pump at a high pressure is interposed in the middle of the detergent channel 39 so as to lift the detergent up to the washing and disinfecting bath 4 from the detergent tank 11a.

The alcohol tank 11b is connected to one end of an alcohol channel 41, and the alcohol channel 41 has the other end connected to the channel block 27 so as to communicate with the channel 21 in a predetermined way.

An alcohol supply pump 42 configured by a self-priming pump at a high pressure for lifting alcohol up to the washing and disinfecting bath 4 from the alcohol tank 11b, and an electromagnetic valve 43 are interposed in the alcohol channel 41.

Further, one end of an air channel 44 is connected to the channel block 27 so as to communicate with the channel 21 in a predetermined way. The air channel 44 is used for supplying air from an air pump 45 configured by a self-priming pump, which can transfer gas, to the suction channel 100i.

The air channel 44 has the other end connected to the air pump 45, and a check-valve 47 and an air filter 46 which is regularly replaced are interposed in the intermediate position of the air channel 44.

A change-over valve 57 capable of being opened and closed for discharging the washing solution or the like to outside and recovering the disinfectant solution to the chemical solution tank 58 by a changing operation of the valve is placed in the water drain port 55 of the washing and disinfecting bath 4.

One end of a water drain channel 59 is connected to and communicating with a water drain hose not illustrated and connected to an external water drain port. The other end of the water drain channel 59 is connected to the change-over valve 57, and a water drain pump 60 configured by a non-self-priming pump is interposed in the water drain channel 59. Further, one end of a chemical solution recovering channel 61 is connected to the change-over valve 57, and the other end of the chemical solution recovering channel 61 is connected to the chemical solution tank 58.

One end of a chemical solution supply channel 62 is connected to the chemical solution tank 58 so as to be supplied with the disinfectant solution from the chemical solution bottle 12a. The other end of the chemical solution supply channel 62 is connected to the cassette tray 12 in a predetermined way.

Further, one end portion with a suction filter 63 being provided, of a chemical solution channel 64 is housed in the chemical solution tank 58 in a predetermined way. The chemical solution channel 64 has the other end connected to the disinfectant solution nozzle 23, and a chemical solution pump 65 configured by a self-priming pump at a high pressure is interposed in the intermediate position in order to lift the disinfectant solution up to the washing and disinfecting bath 4 from the chemical solution tank 58.

For example, the two ultrasound transducers 52 and the heater 53 are placed at the lower portion of the bottom surface 50t of the washing and disinfecting bath 4 as described above. Further, for temperature regulation of the heater 53, a temperature detection sensor 53a is provided in a substantially center of the bottom surface 50t of the washing and disinfecting bath 4.

The heater 53 is for heating the disinfectant solution which is stored in the washing and disinfecting bath 4 and circulates in the apparatus to a predetermined temperature. The disinfectant solution has a proper temperature at which its highest disinfection effect can be expected. The disinfectant solution which is heated to the aforementioned predetermined temperature that is the proper temperature by the heater 53 can effectively disinfect the endoscope 100 and the respective channels in the apparatus main body 2.

Further, the temperature detection sensor 53a detects the liquid temperature of the disinfectant solution which is stored in the washing and disinfecting bath 4, and circulates in the apparatus, and transmits the detection result to a control unit 70. Subsequently, the control unit 70 performs control of driving and stopping the heater 53 so as to keep the disinfectant solution at a predetermined temperature on the basis of the detection result from the temperature detection sensor 53a.

Further, a power supply 71, which is supplied with electric power from an external AC receptable, and the control unit 70, which is electrically connected to the power supply 71, are provided inside the washing and disinfecting apparatus 1. The control unit 70 performs drive control of the aforementioned respective pumps, respective electromagnetic valves, the flow rate sensor 150 and the like by being supplied with various signals from the main operation panel 25 and the sub operation panel 13.

Next, a configuration of connection of the suction channel at the other end side of the washing tube with one end side being connected to the gas supply and water supply/forceps opening port of FIG. 3 to the channel mouthpiece will be described with use of FIGS. 5 to 7.

Figure 5:
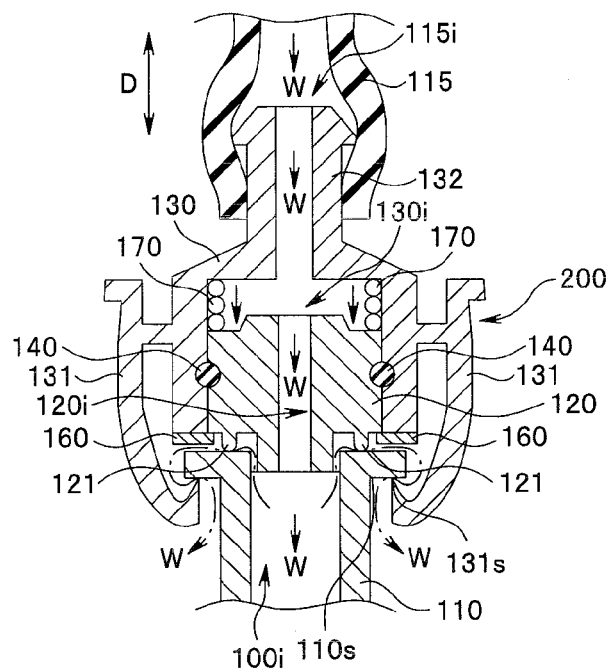
FIG. 5 is a partial cross-sectional view showing a state in which a liquid supply mouthpiece at the other end side of a washing tube is fitted to a channel mouthpiece of a treatment instrument insertion port of the endoscope of FIG. 4 in enlargement.

FIG. 5 is a partial cross-sectional view showing a state in which a liquid supply mouthpiece at the other end side of the washing tube is fitted to the channel mouthpiece of the treatment instrument insertion port of the endoscope of FIG. 4 in enlargement. FIG. 6 is a partial cross-sectional view showing a state in which a locking portion of a claw portion of the liquid supply mouthpiece is locked to a locked portion of the channel mouthpiece of FIG. 5 in enlargement.

Hereinafter, the channel mouthpiece of the suction channel to which the liquid supply mouthpiece is connected will be described by citing the channel mouthpiece 110 as an example.

As shown in FIG. 5, a liquid supply mouthpiece 200 which can be detachably fitted to the channel mouthpiece 110, and supplies a liquid W such as water, a washing solution, and a disinfectant solution in the washing and disinfecting bath 4 which is fed through the circulation channel 20, the channel 21, the port 33 and the washing tube 115 to the suction channel 100i when fitted to the channel mouthpiece 110 is provided at the other end side of the washing tube 115.

The liquid supply mouthpiece 200 also has the function of supplying air which is fed through the air pump 45, the air channel 44, the channel 21, the port 33 and the washing tube 115, to the suction channel 100i in addition to the liquid W.

A main part of the liquid supply mouthpiece 200 is configured by a first channel member 120 and a second channel member 130.

The first channel member 120 is formed into a substantially circular cylindrical shape, and a first channel 120i is formed along an attaching and detaching direction D of the liquid supply mouthpiece 200 to and from the channel mouthpiece 110 inside the first channel member 120. The first channel 120i communicates with the suction channel 100i when the liquid supply mouthpiece 200 is fitted to the channel mouthpiece 110.

Figure 6:
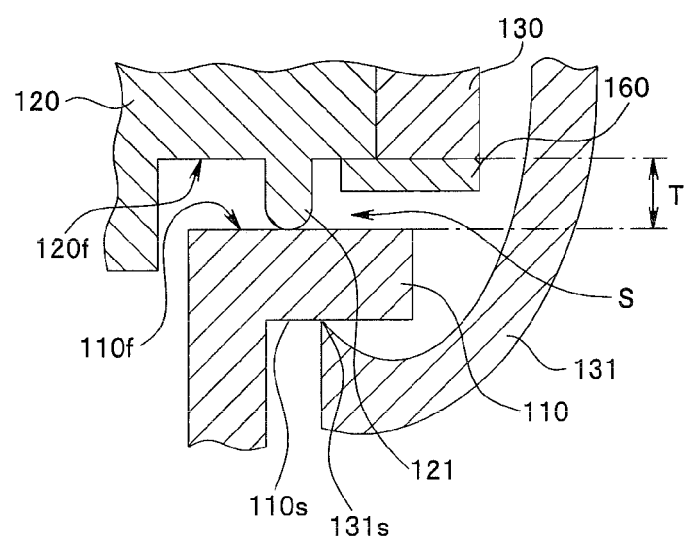
FIG. 6 is a partial cross-sectional view showing a state in which a locking portion of a claw portion of the liquid supply mouthpiece is locked at a locked portion of the channel mouthpiece of FIG. 5 in enlargement.
Figure 7:
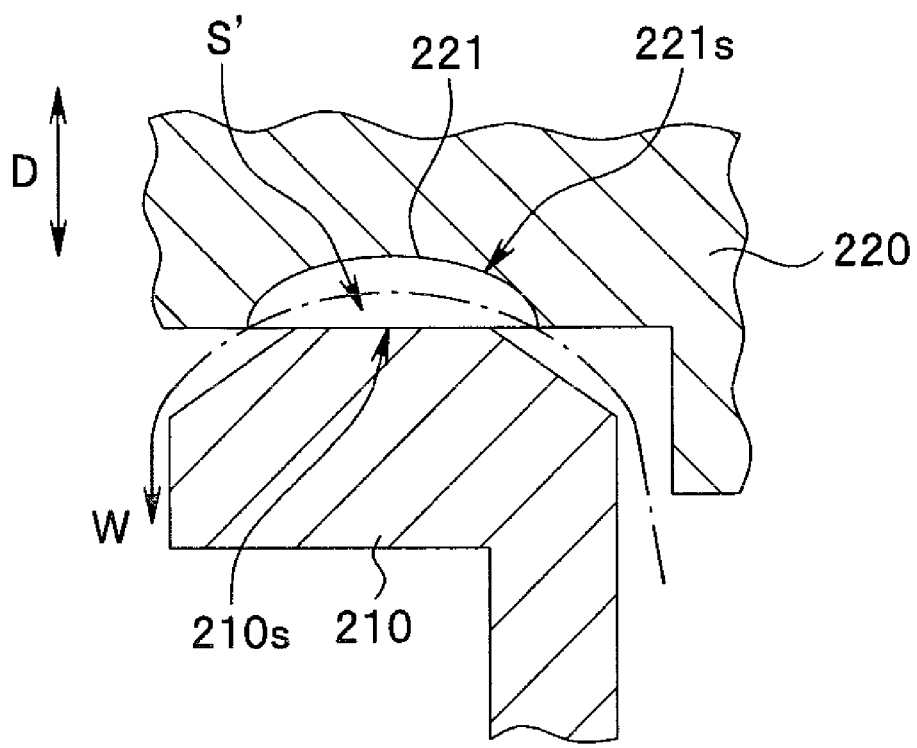
FIG. 7 is a partial cross-sectional view showing a modified example in which a space is provided between the channel mouthpiece and the liquid supply mouthpiece by the configuration differing from FIG. 5.

Further, in the first channel member 120, for example, two projection portions 121 which abut on a fitting surface 110f at an upper side in the attaching and detaching direction in FIG. 5 of the channel mouthpiece 110 when the liquid supply mouthpiece 200 is fitted onto the channel mouthpiece 110 are formed at a part of a bottom portion side in the attaching and detaching direction D in FIG. 5 as shown in FIGS. 5 and 6.

Thereby, when the liquid supply mouthpiece 200 is fitted to the channel mouthpiece 110, only a part at the bottom portion side in the attaching and detaching direction D of the first channel member 120 abuts on the fitting surface 110f.

Further, since the projection portions 121 abut on the fitting surface 110f, a space S having a set clearance T in the attaching and detaching direction D is formed between the fitting surface 110f and an opposing surface 120f except for the projection portions 121 in the bottom portion side of the first channel member 120, as shown in FIG. 6. In other words, the projection portions 121 are formed to have such a length that the space S has the set clearance T in the attaching and detaching direction D.

Therefore, as a result of the space S being formed between the fitting surface 110f and the opposing surface 120f, as shown in FIG. 5, when the liquid supply mouthpiece 200 is fitted onto the channel mouthpiece 110 and the liquid W is supplied to the suction channel 100i, a set amount of the liquid W leaks at a fixed rate from the suction channel 100i through the space S. Thereby, the fitting surface 110f and the opposing surface 120f are reliably washed and disinfected by the liquid W which leaks from the space S except for abutting portions of the projection portion 112 and the fitting surface 110f.

The set rate of the liquid W which leaks out of the space S is set to be higher than a rate of 0 L/min and not over a rate of 1.5 L/min (0<W≦1.5). In other words, the set clearance T is set to be the clearance from which the liquid W leaks from the space S at a rate higher than the rate of 0 L/min and not over 1.5 L/min. Further, the abovementioned "higher than the rate of 0 L/min" means "not including the rate of 0 L/min."

A second channel member 130 is fitted on an outer periphery of the first channel member 120 via an O-ring 140 as shown in FIG. 5, and is formed into a substantially convex shape in section. Further, a second channel 130i which communicates with the first channel 120i is formed inside the second channel member 130.

Further, the second channel 130i is provided with a pressing member 170 such as, for example, a spring, which presses the first channel member 120 to the channel mouthpiece 110 side in the attaching and detaching direction D in the second channel 130i when the liquid supply mouthpiece 200 is fitted onto the channel mouthpiece 110.

The pressing member 170 has a function of keeping the set clearance T between the fitting surface 110f and the opposing surface 120f by pressing the first channel member 120 to the channel mouthpiece 110 side so that the projection portions 121 always abut on the fitting surface 110f when the liquid supply mouthpiece 200 is fitted onto the channel mouthpiece 110.

The pressing force of the pressing member 170 is set at the pressing force that prevents the first channel member 120 from moving upward in the attaching and detaching direction D in the second channel 130i and causing the projection portions 121 to separate from the fitting surface 110f by the pressure applied to the first channel member 120 from the suction channel 100i when the liquid supply mouthpiece 200 is fitted onto the channel mouthpiece 110 and the liquid W is supplied to the suction channel 100i. More specifically, the pressing force is set at the pressing force which keeps the set clearance T. The pressure which is applied to the first channel member 120 by the suction channel 100i differs depending on the channel diameter of the suction channel 100i.

Further, a holding member 160 which holds the first channel member 120 in the second channel 130i is provided at the bottom portion side in the attaching and detaching direction D of the second channel member 130.

Returning to FIG. 5, for example, two claw portions 131, which are locking portions, are formed at an outer periphery of the second channel member 130. The claw portion 131 has a function of fixing the second channel member 130 to the channel mouthpiece 110 with pressing force of the pressing member 170 by a locking claw 131s being locked to a locked portion 110s formed on the surface of the channel mouthpiece 110 at the bottom portion side in the attaching and detaching direction D as shown in FIGS. 5 and 6 when the liquid supply mouthpiece 200 is fitted onto the channel mouthpiece 110. Namely, by the claw portion 131, the liquid supply mouthpiece 200 is prevented from being separated from the channel mouthpiece 110.

Further, a liquid introduction port 132, which is inserted in a flow passage 115i inside the washing tube 115 to be fluid-tight and introduces the liquid W flowing in the flow passage 115i of the washing tube 115 into the second channel 130i, is formed at an upper side in the attaching and detaching direction D, of the second channel member 130.

The liquid supply mouthpiece not illustrated which is fitted onto the channel mouthpiece 111 also has the same configuration as the abovementioned liquid supply mouthpiece 200.

Next, an operation of the present embodiment will be described. Hereinafter, only the operation of washing the suction channel and detecting clogging of the suction channel will be described. The other operations are known, and therefore, description of them will be omitted.

When the suction channel 100i of the endoscope 100 set in the washing and disinfecting bath 4 is washed, the liquid supply mouthpiece 200 provided at the other end side of the washing tube 115 with the one end being connected to the port 33 is fitted onto the channel mouthpiece 110 of the endoscope 100 first as shown in FIG. 5.

At this time, as shown in FIGS. 5 and 6, the locking claw 131s of the claw portion 131 is locked to the locked portion 110s of the channel mouthpiece 110, whereby unexpected separation of the liquid supply mouthpiece 200 from the channel mouthpiece 110 is prevented, and the projection portions 121 of the first channel member 120 about on the fitting surface 110f of the channel mouthpiece 110. Thereby, the space S having the set clearance T in the attaching and detaching direction D is formed between the fitting surface 110f and the opposing surface 120f.

Further, as shown in FIG. 5, the flow passage 115i of the washing tube 115 communicates with the suction channel 100i through the second channel 130i and the first channel 120i of the liquid supply mouthpiece 200.

Thereafter, the tap water from the faucet 5 is supplied to the washing and disinfecting bath 4 from the water supply circulation nozzle 24 through the water supply channel 9, and by the detergent pump 40 being driven, the detergent from the detergent tank 11a is supplied to the washing and disinfecting bath 4 from the detergent nozzle 22 through the detergent channel 39. As a result, a washing solution is diluted with the tap water, and thereby, the washing and disinfecting bath 4 is filled with the washing solution.

Thereafter, when the liquid flow pump 19 is driven, the washing solution in the washing and disinfecting bath 4 is supplied to the washing and disinfecting bath 4 again from the water supply circulation nozzle 24 through the circulation channel 20 and the liquid flow channel 18 from the circulation port 56. As a result, convection of the washing solution occurs in the washing and disinfecting bath 4, and thereby, the outer surface of the endoscope 100 is washed.

Next, when the channel pump 26 is driven, the washing solution in the washing and disinfecting bath 4 is supplied to the suction channel 100i from the channel mouthpiece 110 from the circulation port 56 through the circulation channel 20, the channel 21, the port 33, the washing tube 115, and the liquid supply mouthpiece 200. As a result, the suction channel 100i is washed.

At this time, as shown in FIG. 5, the first channel member 120 is pressed to the channel mouthpiece 110 side along the attaching and detaching direction D by the pressing member 170, and therefore, the set clearance T along the attaching and detaching direction D, of the space S formed by abutment of the projection portions 121 on the fitting surface 110f is kept even if pressure is applied to the first channel member 120 from the suction channel 100i.

Further, through the space S, a fixed amount of the washing solution leaks outside the channel mouthpiece 110. The leaking rate at this time is set to be higher than the rate of 0 L/min amount and not over the rate of 1.5 L/min. As a result, the fitting surface 110f and the opposing surface 120f except for the abutting portions of the projection portions 121 are washed by the washing solution which leaks out.

Further, with supply of the washing solution to the suction channel 100i, the flow rate sensor 150 provided in the channel 21 detects the rate of the flow passing in the channel 21, and compares the flow rate without clogging in the suction channel 100i and the present flow rate, thereby detecting whether or not clogging occurs to the suction channel 100i.

When the flow rate without clogging in the suction channel 100i and the present flow rate substantially match with each other, it is determined that there is no clogging in the suction channel 100i, and the determination result is transmitted to the control unit 70. Further, when the present flow rate is lower than the flow rate without clogging in the suction channel 100i, it is determined that clogging occurs to the suction channel 100i, and the determination result is transmitted to the control unit 70.

There is usually the problem that the flow rate change in the flow rate sensor 150 cannot be detected when the washing solution leaks from the respective mouthpieces 110 and 200 as described above. However, the present embodiment is configured so that the washing solution leaks out of the space S between the respective mouthpieces 110 and 200 at a fixed rate, more specifically, at a rate higher than the rate of 0 L/min and not over the rate of 1.5 L/min, and therefore, the flow rate sensor 150 can reliably detect the flow rate change.

Finally, after the suction channel 100i is washed, tap water is stored in the washing and disinfecting bath 4 by known means, and thereafter, the tap water is supplied to the suction channel 100i, whereby the suction channel 100i is rinsed. After the disinfectant solution is stored in the washing and disinfecting bath 4 by known means, and the disinfectant solution is supplied to the suction channel 100i, the suction channel 100i is disinfected. Thereafter, alcohol and air are supplied to the suction channel 100i by known means, and the suction channel 100i is dried. The operation described above is not limited to the channel mouthpiece 110, but is applied similarly to the channel mouthpiece 111.

Thus, the present embodiment is described as configured so that the liquid W at a set rate, more specifically, at a rate amount higher than the rate of 0 L/min and not over the rate of 1.5 L/min leaks out of the space S between the fitting surface 110f and the opposing surface 120f of the liquid supply mouthpiece 200 as a result of the projection portions 121 abutting on the fitting surface 110f of the channel mouthpiece 110 when the liquid supply mouthpiece 200 is fitted onto the channel mouthpiece 110.

Further, it is described that clogging of the suction channel 100i is detected from change in the supply rate of the liquid W by the flow rate sensor 150 provided in the channel 21.

According to this, when the suction channel 100i is washed and disinfected, the fitting surface 110f and the opposing surface 120f other than the portions where the projection portions 121 abut can also be washed and disinfected reliably by the liquid W leaking out of the space S.

Further, the liquid W is configured to leak out of the space S at a fixed rate, and therefore, when clogging occurs to the suction channel 100i, change in the flow rate in the flow rate sensor 150 can be reliably detected.

Further, it is described that in the present embodiment, when the liquid supply mouthpiece 200 is fitted onto the channel mouthpiece 110, the pressing member 170 presses the first channel member 120 to the channel mouthpiece 110 side in the attaching and detaching direction D, whereby the set clearance T between the fitting surface 110f and the opposing surface 120f is kept.

According to this, even if the pressure is applied to the first channel member 120 from the suction channel 100i with supply of the liquid W to the suction channel 100i, the set clearance T does not change. Therefore, the flow rate of the liquid W which leaks out of the space S can be kept constant, and therefore, detection of the change in the flow rate in the flow rate sensor 150 is not hindered.

From the above, the endoscope washing and disinfecting apparatus 1 including the configuration which can reliably wash and disinfect the fitting surface 110f and the opposing surface 120f between the channel mouthpiece 110 of the suction channel 100i and the liquid supply mouthpiece 200 by leakage of the liquid W from the space between the respective mouthpieces 110 and 120, and can detect clogging of the suction channel 100i accurately and reliably can be provided.

Hereinafter, a modified example will be shown.

In the present embodiment, the endoscope channel is described with the suction channel cited as an example, but the endoscope channel is not limited thereto, and the present embodiment may be naturally applied to the other channels included by the endoscope, for example, the gas supply and water supply channel.

Further, in the present embodiment, it is described that the endoscope including the operation section 101, the universal cord 102, the connector 103 and the insertion section 104 is cited as an example of the endoscope 100, and the suction channel 100i provided in the respective sections 101 to 104 is washed. However, the endoscope is not limited thereto, but the present embodiment may be applied to the case of washing the suction channel provided in the insertion section and the operation section, in the endoscope which does not have the universal cord 102 and the connector 103.

Further, hereinafter, a modified example will be shown with use of FIG. 7. FIG. 7 is a partial cross-sectional view showing a modified example in which a space is provided between the channel mouthpiece and the liquid supply mouthpiece by the configuration differing from FIG. 5.

In the present embodiment, it is described that the projection portions 121 of the liquid supply mouthpiece 200 abut on the fitting surface 110f of the channel mouthpiece 110, whereby the space S is formed between the opposing surface 120f of the liquid supply mouthpiece 200 and the fitting surface 110f of the channel mouthpiece 110, and the liquid W leaks out of the suction channel 100i through the space S.

However, this is not restrictive. As shown in FIG. 7, a fitting surface 210s of a channel mouthpiece 210 at the top surface side in the attaching and detaching direction D is provided to be in a substantially mound shape, and a hole portion 221 not in contact with the fitting surface 210s is provided at a part of a bottom portion side of the liquid supply mouthpiece 200, whereby a space S' is formed between an opposing surface 221s to the fitting surface 210s in the hole portion 221 and the fitting surface 210s of the channel mouthpiece 210, and the liquid W may be caused to leak out of the suction channel 100i through the space S'.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. A liquid supply mouthpiece, comprising:
a first channel member in which a projection portion of the first channel member abuts on a fitting surface in a channel mouthpiece of an endoscope, and a first channel internally provided communicates with an endoscope channel in the channel mouthpiece when the liquid supply mouthpiece is fitted onto the channel mouthpiece of the endoscope, the projection portion projecting from an opposing surface opposed to the fitting surface toward the channel mouthpiece of the endoscope, and the fitting surface being opposed to the liquid supply mouthpiece;
a second channel member which is fitted on and fixed to an outer periphery of the first channel member and is internally provided with a second channel which communicates with the first channel;
a pressing member which is provided in the second channel, and presses the first channel member toward the channel mouthpiece of the endoscope in the second channel when the liquid supply mouthpiece is fitted to the channel mouthpiece of the endoscope; and
a liquid introduction port which is formed in the second channel member and introduces the liquid into the second channel.

2. The liquid supply mouthpiece according to claim 1, further comprising: a locking portion which is formed at the second channel member, fixes the second channel member to the channel mouthpiece of the endoscope with pressing force of the pressing member when the liquid supply mouthpiece is fitted to the channel mouthpiece of the endoscope, and is locked to a locked portion provided on an outer periphery of the channel mouthpiece of the endoscope.

3. The liquid supply mouthpiece according to claim 1, wherein the projection portion of the first channel member abuts on the fitting surface of the channel mouthpiece of the endoscope, and thereby, a space having a set clearance is provided between the opposing surface of the first channel member and the fitting surface.

4. The liquid supply mouthpiece according to claim 3, wherein the pressing member keeps the set clearance of the space by pressing the first channel member to the channel mouthpiece of the endoscope.

5. An endoscope washing and disinfecting apparatus, comprising:
a liquid supply mouthpiece which is fitted onto a channel mouthpiece of an endoscope, supplies at least a liquid to an endoscope channel inside the endoscope, and automatically washes and disinfects the endoscope channel, the channel mouthpiece being provided at an insertion port for the endoscope channel inside the endoscope, the liquid supply mouthpiece including:
a first channel member in which a projection portion of the first channel member abuts on a fitting surface in the channel mouthpiece of the endoscope, and a first channel internally provided communicates with the endoscope channel inside the channel mouthpiece, when the liquid supply mouthpiece is fitted onto the channel mouthpiece of the endoscope, the projection portion projecting from an opposing surface opposed to the fitting surface toward the channel mouthpiece of the endoscope, and the fitting surface being opposed to the liquid supply mouthpiece;

a second channel member which is fitted and fixed to an outer periphery of the first channel member, and is internally provided with a second channel which communicates with the first channel;

a pressing member which is provided in the second channel, and presses the first channel member toward the channel mouthpiece of the endoscope in the second channel when the liquid supply mouthpiece is fitted onto the channel mouthpiece of the endoscope; and a liquid introduction port which is formed in the second channel member and introduces the liquid to the second channel.

6. The endoscope washing and disinfecting apparatus according to claim 5, further comprising: a locking portion which is formed at the second channel member, fixes the second channel member to the channel mouthpiece of the endoscope with pressing force of the pressing member when the liquid supply mouthpiece is fitted onto the channel mouthpiece of the endoscope, and is locked to a locked portion provided on an outer periphery of the channel mouthpiece of the endoscope.

7. The endoscope washing and disinfecting apparatus according to claim 5, further comprising:

a liquid supply channel which is connected to the liquid introduction port and supplies the liquid to the second channel; and a flow rate sensor which is provided in the liquid supply channel, detects a supply rate of the liquid, and detects clogging of the endoscope channel from the supply rate of the liquid.

8. The endoscope washing and disinfecting apparatus according to claim 7, wherein the projection portion of the first channel member abuts on the fitting surface of the channel mouthpiece of the endoscope, and thereby, a space having a set clearance in an attaching and detaching direction of the liquid supply mouthpiece is provided between the opposing surface opposed to the fitting surface of the first channel member and the fitting surface of the channel mouthpiece, and when the liquid is supplied to the channel mouthpiece of the endoscope from the liquid supply mouthpiece, the liquid leaked out of the endoscope channel at a set flow rate is supplied on the fitting surface of the channel mouthpiece and the opposing surface of the first channel member through the space.

9. The endoscope washing and disinfecting apparatus according to claim 8, wherein the endoscope channel is a suction channel which sucks a target object of an examined region when the endoscope is inserted into the examined region, and the set rate of the liquid which leaks out of the suction channel through the space when the liquid is supplied to the suction channel is set to be higher than a rate of 0 L/min and not over a rate of 1.5 L/min.

10. The endoscope washing and disinfecting apparatus according to claim 9, wherein the flow rate sensor detects a rate of flow flowing in the liquid supply channel in a state in which the liquid leaks from the endoscope channel at a flow rate which is higher than a rate of 0 L/min and not over a rate of 1.5 L/min, compares a flow rate without clogging in the liquid supply channel and a present flow rate, determines that there is no clogging when there is no change in flow rate, and detects clogging of the liquid supply channel when the present flow rate decreases.

11. The endoscope washing and disinfecting apparatus according to claim 8, wherein the flow rate sensor detects a rate of flow flowing in the liquid supply channel in a state in which the liquid leaks out at a set flow rate from the endoscope channel, compares a flow rate without clogging in the liquid supply channel and a present flow rate, determines that there is no clogging when there is no change in flow rate, and detects clogging of the liquid supply channel when the present flow rate decreases.

12. The endoscope washing and disinfecting apparatus according to claim 5, wherein the projection portion of the first channel member abuts on the fitting surface of the channel mouthpiece of the endoscope, and thereby, a space having a set clearance in an attaching and detaching direction of the liquid supply mouthpiece is provided between the opposing surface opposed to the fitting surface of the first channel member and the fitting surface of the channel mouthpiece, and when the liquid is supplied to the channel mouthpiece of the endoscope from the liquid supply mouthpiece, the liquid leaked out of the endoscope channel at a set flow rate is supplied on the fitting surface of the channel mouthpiece and the opposing surface of the first channel member through the space.

13. The endoscope washing and disinfecting apparatus according to claim 12, wherein the pressing member keeps the set clearance of the space by pressing the first channel member to the channel mouthpiece side of the endoscope.

14. The endoscope washing and disinfecting apparatus according to claim 12, wherein the endoscope channel is a suction channel which sucks a target object of an examined region when the endoscope is inserted into the examined region, and the set flow rate of the liquid which leaks out of the suction channel through the space when the liquid is supplied to the suction channel is set to be higher than the rate of 0 L/min and not over the rate of 1.5 L/min.

* * * * *